United States Patent [19]
Goeringer

[11] Patent Number: 5,811,108
[45] Date of Patent: Sep. 22, 1998

[54] SUN BLOCKING TATTOO STICKER

[76] Inventor: Leslie A. Goeringer, 6801 Buttermere La., Bethesda, Md. 20817-1529

[21] Appl. No.: 683,595

[22] Filed: Jul. 15, 1996

Related U.S. Application Data

[63] Continuation-in-part of Ser. No. 494,389, Jun. 26, 1995, abandoned.
[51] Int. Cl.⁶ .................................. A61K 7/00; A61K 9/70
[52] U.S. Cl. ......................... 424/401; 424/443; 424/448; 424/402
[58] Field of Search .................................. 424/401, 402, 424/443, 448, 59, 445; 428/343

[56] References Cited

U.S. PATENT DOCUMENTS 2,851,805  9/1958  Allen ............................................ 41/10

*Primary Examiner*—Thurman K. Page
*Assistant Examiner*—Sharon Howard

[57] ABSTRACT

A shielding web that is transparent and blocks ultraviolet light from irradiating selected portions of human skin. The shielding web has a pressure sensitive adhesive applied to a rear surface thereof which can be utilized to adhesively couple the web to human skin. The web is comprised of a material the precludes tanning of the covered skin.

2 Claims, 3 Drawing Sheets

SUN BLOCKING TATTOO STICKER

BACKGROUND OF THE INVENTION

This application is a Continuation-in-Part of U.S. Pat. application Ser. No. 08/494,389, filed Jun. 26, 1995.

1. Field of the Invention

The present invention relates to a sun blocking tattoo sticker and more particularly pertains to providing radiation shielding structures for blocking ultraviolet light from irradiating selected portions of human skin.

2. Description of the Prior Art

The use of a radiation shielding structure is known in the prior art. More specifically, radiation shielding structures heretofore devised and utilized for the purpose of skin shielding are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,990,339 to Scholl, Simmons and Bunnelle disclose a dermal treatment film. U.S. Pat. No. 4,894,222 to Matravers discloses a waterproof sunscreen. Other known prior art radiation shielding structures include U.S. Pat. No. 5,313,666; U.S. Pat. No. 5,052,418; U.S. Pat. No. 4,055,249; U.S. Pat. No. 2,033,139; U.S. Pat. Design No. 342,283; and U.S. Pat. Design No. 285,155.

While these devices fulfill their respective, particular objectives and requirements, the aforementioned patents do not describe sun blocking tattoo sticker that blocks ultraviolet light from irradiating selected portions of human skin which includes a shielding web having pressure sensitive adhesive applied to a rear surface for coupling the wed to human skin.

In this respect, the Sun blocking tattoo sticker according to the present invention substantially departs from the conventional concepts and designs of the prior art, and in doing so provides an apparatus primarily developed for the purpose of providing radiation shielding structures for blocking ultraviolet light from irradiating selected portions of human skin.

Therefore, it can be appreciated that there exists a continuing need for a new and improved Sun blocking tattoo sticker which can be used for providing radiation shielding structures for blocking ultraviolet light from irradiating selected portions of human skin. In this regard, the present invention substantially fulfills this need.

SUMMARY OF THE INVENTION

In view of the foregoing disadvantages inherent in the known types of radiation shielding structures now present in the prior art, the present invention provides an improved sun blocking tattoo sticker. As such, the general purpose of the present invention, which will be described subsequently in greater detail, is to provide a new and improved sun blocking tattoo sticker and method which has all the advantages of the prior art and none of the disadvantages.

To attain this, the present invention essentially comprises a shielding means for coupling to skin of a human body. The shielding means is for shielding a pre-determined and patterned covered portion of the skin from ultraviolet light. The shielding means comprises a visible-light transparent and substantially ultraviolet opaque web material. The web material has a transparent pressure sensitive adhesive coupled to a rear surface thereof. The shielding means operating to absorb at least ninety percent of ultraviolet light in the 300 to 380 nanometer range while transmitting substantially all visible light therethrough.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sun blocking tattoo sticker which has all of the advantages of the prior art Radiation shielding structures and none of the disadvantages.

It is another object of the present invention to provide a new and improved sun blocking tattoo sticker which may be easily and efficiently manufactured and marketed.

It is further object of the present invention to provide a new and improved sun blocking tattoo sticker which is of durable and reliable constructions.

An even further object of the present invention is to provide a new and improved sun blocking tattoo sticker which is susceptible of a low cost of manufacture with regard to both materials and labor, and which accordingly is then susceptible of low prices of sale to the consuming public, thereby making such sun blocking tattoo sticker economically available to the buying public.

Even still another object of the present invention is to provide a sun blocking tattoo sticker for providing radiation shielding structures for blocking ultraviolet light from irradiating selected portions of human skin.

Lastly, it is an object of the present invention to provide a new and improved sun blocking tattoo sticker including a shielding web that is transparent and blocks ultraviolet light from irradiating selected portions of human skin. The shielding web has a pressure sensitive adhesive applied to a rear surface thereof which can be utilized to adhesively couple the web to human skin. The web is comprised of a material the precludes tanning of the covered skin.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
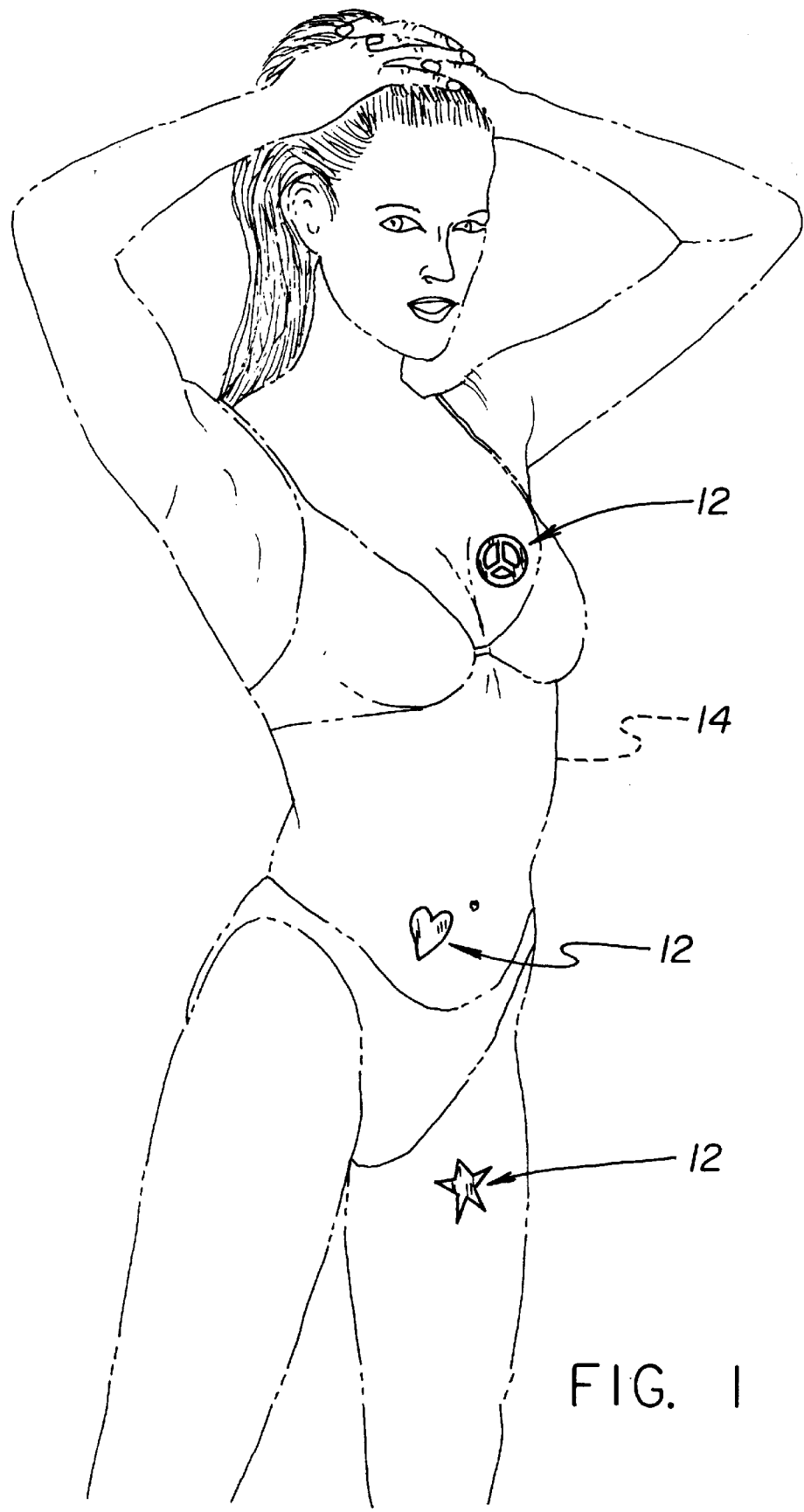
FIG. 1 is an isometric illustration of a plurality of sun blocking tattoo stickers constructed and in use in accordance with the principles of the present invention.

With reference now to the drawings, and in particular to FIGS. 1–4 thereof, the preferred embodiment of the new and improved sun blocking tattoo sticker embodying the principles and concepts of the present invention and generally designated by the reference numeral 10 will be described.

More specifically, it will be noted that the sun blocking tattoo sticker 10 is comprised of a plurality of components. Such components in their broadest context include a shielding means 12 for coupling to skin of a human body 14 and for shielding a covered portion of the skin from ultraviolet light. By this structure, the shielding means 12 operates to preclude ultraviolet light induced tanning of the covered areas of skin of the associated human body 14.

Figure 4:
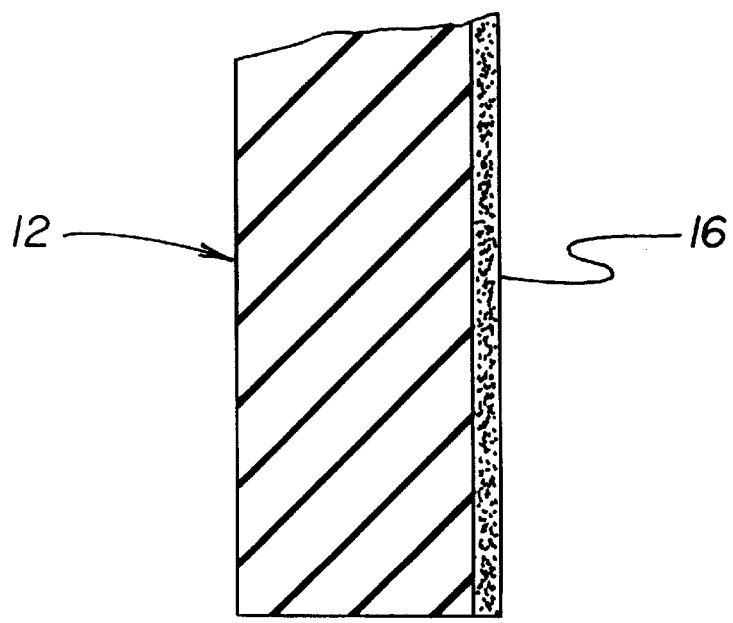
FIG. 4 is a cross-sectional view taken along line 4—4 of FIG. 3.

Specifically, as shown in FIG. 4, the shielding means 12 is preferably comprised of a material web having a pressure sensitive adhesive 16 coupled to a rear surface thereof. The shielding means couples to the skin for shielding a predetermined and patterned covered portion of the skin form ultraviolet light. The pressure sensitive adhesive 16 operates to removably couple the material web to skin of the human body 14, as shown in FIG. 1. The material web preferably comprised of a flexible polymeric material which is substantially transparent relative to visible light, yet substantially opaque relative to ultraviolet radiation.

Preferably, the material web is made of a polymer having uniformly distributed therethrough an ultraviolet light absorbing amount of 2-(hydroxy-lower alkyl phenyl) benzotriazole which may be halogen substituted in the four, five, six, or seven positions. The amount of benzotriazole distributed throughout the polymer is preferably from about 0.01 to about 5 parts by weight of the polymer. The ultraviolet light absorbing substance may be mixed with the monomers and then the monomers polymerized, or by compounding with the polymer prior to extrusion or molding of the material web of the shielding means 12. Such composition of the material web results in a shielding means 12 operable to absorb at least ninety percent of ultraviolet light in the 300 to 380 nanometer range, while transmitting substantially all visible light therethrough. By this structure, the shielding means 12 is substantially transparent to an individual viewing the shielding means, thereby facilitating inconspicuous use of the device 10 when applied to a human body 14.

The pressure sensitive adhesive 16 of the present invention 10 is preferably substantially transparent so as to cooperate with the visible light transparent material web of the shielding means 12 to cause the entire device 10 to appear transparent to visible light. Examples of suitable transparent adhesives for use with the present invention are disclosed in the U.S. Pat. Nos. 3,923,757; 4,068,028; 4,137,364; and 5,143,995, all of which are incorporated herein by reference.

Figure 2:
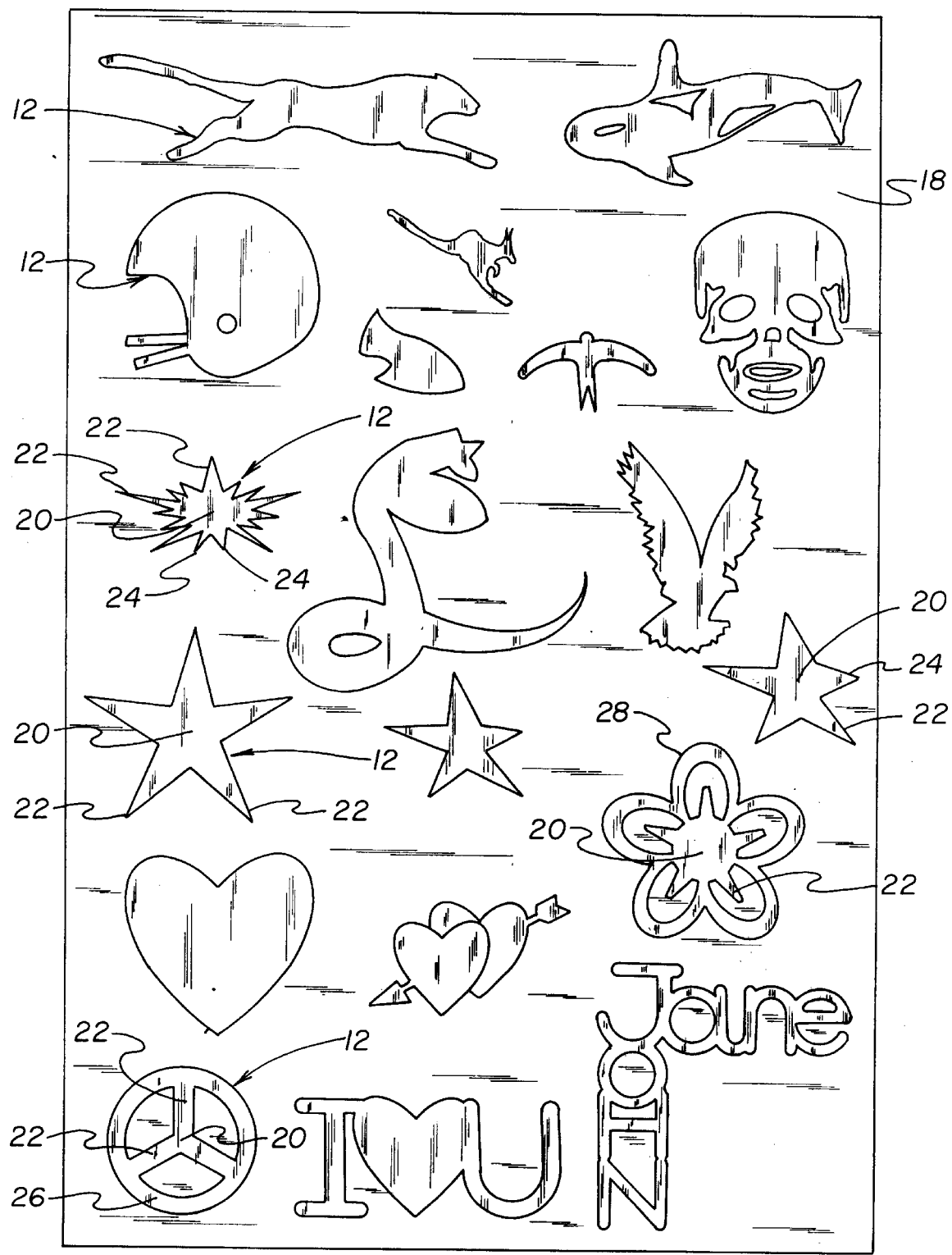
FIG. 2 is an elevational view of the present invention.
Figure 3:
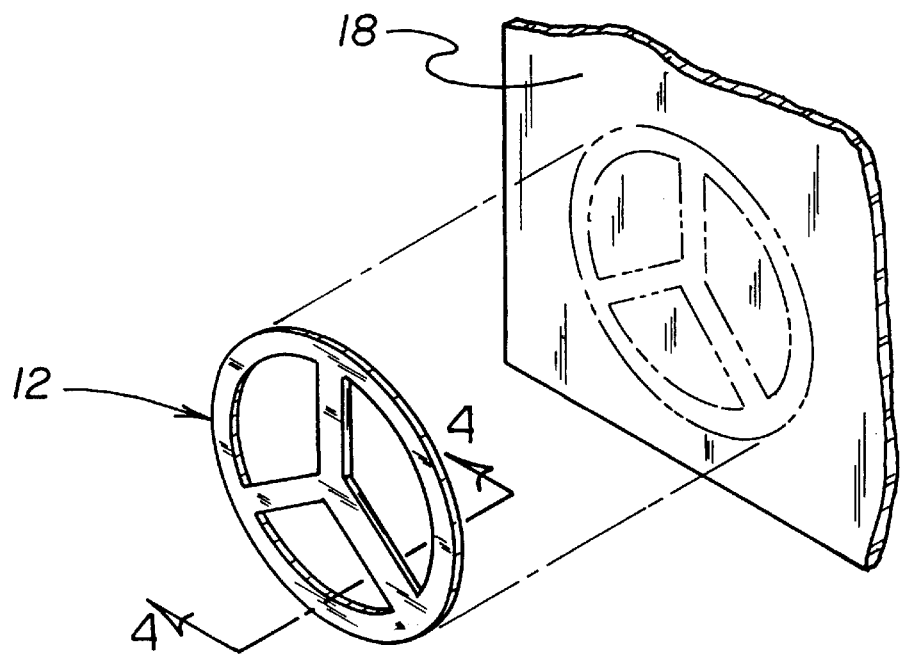
FIG. 3 is an exploded isometric illustration of a portion of the present invention.

Referring now to FIGS. 2 and 3, it can be shown that the present invention 10 preferably comprises a sheet 18 having a plurality of disparately shaped shielding means 12 coupled thereto fro selection and subsequent removal therefrom by an end user of the device. A preferred shape of the shielding means 12 is illustrated in FIG. 2 and comprises the material web being shaped so as to define a center web 20 having a plurality of first elongated projection webs 22 extending from the center web in a radially outward direction. A plurality of second elongated projection webs 24 can also project radially outward from the center web between adjacent first elongated projection webs 22. Preferably, the first elongated projection webs extend a first distance from the center web, with the second elongated projection webs projecting a second distance for the center web, wherein the first distance is substantially greater than the second distance as shown in the drawings. In lieu of the second elongated projection webs 24, the material web may e shaped so as to define an annular outer web 26 extending circumferentially about the center web 20 and coupled to outer distal ends of the first elongated projection webs.

Alternatively, the material web may be shaped so as to define a plurality of U-shaped loop webs 28 that have spaced ends coupled to the center web 20. The U-shaped loop webs extending about the first elongated projection webs 22 so as to define a space between an outer distal end of the first elongated projection webs and the U-shaped loop webs. By this structure, the center web 20 cooperates with the first elongated projection webs and the second elongated projection webs, the annular outer web 26, or the U-shaped loop webs 28 to create a desired pattern of block ultraviolet radiation relative to the skin of the human body 14 to which the device 10 is attached.

As shown in FIG. 3, each of the shielding means 12 coupled to the sheet 18 can be selectively removed therefrom for subsequent application to the human body 14 as shown in FIG. 1. To this end, the sheet is preferably composed of a material permitting removable coupling of the pressure sensitive adhesive 16 relative thereto. Examples of such materials for use in the sheet include wax pater, plastic sheets, or like material.

In use the method of blocking ultraviolet light from irradiating selected portions of human skin to form disparate shapes on areas of the skin is easy to accomplish. The end user will review a sheet of disparately shaped adhesive coated material webs. The end user will remove a first of the disparately shaped material webs from the sheet. The first of the disparately shaped material webs is adhered to the human skin for shielding the skin area under the material web from ultraviolet radiation. If the end user wants several patterns of untanned skin from using the device 10, a second of the disparately shaped material webs is removed from the sheet. The second disparately shaped material webs is adhered to the human skin for shielding the skin area under the material web from ultraviolet radiation. This process of removing the material webs form the sheet and adhering the material webs is continued until all the desired areas of the human skin have at least one of the material webs thereon. The end user then exposing the human skin to visible and non-visible light for a period of five plus minutes with the material webs positioned on all the desired areas of the human skin. The material webs, positioned on the skin, are transparent to visible light and opaque to ultraviolet radiation. The material webs are invisible to the human eye. Finally, the first, second and other material webs are removed from the human skin for exposing the shielded skin area under the material web. Removing the material webs allows the disparate shapes, having been formed on the human skin under the material webs, to be seen by the end user and surrounding individuals.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A sun blocking tattoo sticker comprising,:
    a sheet of disparately shaped shielding means with the shielding means being removable therefrom;
        the shielding means for coupling to skin of a human body and for shielding a pre-determined and patterned covered portion of the skin from ultraviolet light, the shielding means comprising a material web being formed from a polymer being of 2-(hydroxy-lower alkyl phenyl) benzotriazole and visibably light transparent and substantially ultraviolet opaque, a transparent pressure sensitive adhesive coupled to a rear surface of the material web, the shielding means operating to absorb at least ninety percent of ultraviolet light in the 300 to 380 nanometer range while transmitting substantially all visible light therethrought, the shielding means being substantially transparent to an individual viewing for facilitating inconspicuous use thereof.

2. A method for blocking ultraviolet light from irradiating selected portions of human skin for forming disparate shapes on areas of the skin, which comprises the steps of:
    reviewing a sheet of disparately shaped adhesive coated material webs formed of a polymer having uniformly distributed therethrough an ultraviolet light absorbing amount of 2-(hydroxy-lower alkyl phenyl) benzotriazole;
    removing a first of the disparately shaped material webs from the sheet;
    adhering the first of the disparately shaped material webs to the human skin for shielding the skin area under the material web from ultraviolet radiation;
    removing a second of the disparately shaped material webs from the sheet;
    adhering the second of disparately shaped material webs to the human skin for shielding the skin area under the material web from ultraviolet radiation;
    removing a third of the disparately shaped material webs from the sheet;
    adhering the third of the disparately shaped material webs to the human skin for shielding the skin area under the material web from ultraviolet radiation;
    continuing the steps of removing the material webs from the sheet and adhering the material webs until all the desired areas of the human skin have at least one of the material webs thereon;
    exposing the human skin to visible and non-visible light for a period of five plus minutes with the material webs positioned on all the desired areas of the human skin, the material webs being transparent to visible light and opaque to ultraviolet radiation, and the material webs being invisible to the human eye; and
    removing the first, second, third and other material webs from the human skin for exposing the shielded skin area under the material web and allowing the disparate shapes having been formed there on to be seen.

* * * * *